US 9,320,856 B2

(12) United States Patent
Ang (10) Patent No.: US 9,320,856 B2
(45) Date of Patent: *Apr. 26, 2016

(54) SYRINGE ASSEMBLY AND A NEEDLE UNIT FOR ATTACHMENT TO A SYRINGE UNIT TO FORM A SYRINGE ASSEMBLY

(71) Applicant: Intuitive Creations Pte. Ltd, Singapore (SG)

(72) Inventor: Teoh Hwa Ang, Singapore (SG)

(73) Assignee: Intuitive Creations Pte. Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 14/516,571

(22) Filed: Oct. 16, 2014

(65) Prior Publication Data

US 2015/0038942 A1 Feb. 5, 2015

Related U.S. Application Data

(63) Continuation-in-part of application No. 14/494,602, filed on Sep. 24, 2014, which is a continuation of application No. 13/696,617, filed as application No. PCT/SG2010/000492 on Dec. 31, 2010, now Pat. No. 8,864,706.

(60) Provisional application No. 61/373,926, filed on Aug. 16, 2010, provisional application No. 61/332,270, filed on May 7, 2010.

(51) Int. Cl.
*A61M 5/32* (2006.01)
*A61M 5/34* (2006.01)
*A61M 5/50* (2006.01)

(52) U.S. Cl.
CPC ........... *A61M 5/3202* (2013.01); *A61M 5/3234* (2013.01); *A61M 5/347* (2013.01); *A61M 5/508* (2013.01); *A61M 5/5086* (2013.01); *A61M 2005/3239* (2013.01); *A61M 2205/586* (2013.01)

(58) Field of Classification Search
CPC . A61M 5/3202; A61M 5/3234; A61M 5/347; A61M 5/508; A61M 5/086; A61M 2205/586
USPC ......... 604/195, 110, 111, 198, 192, 187, 263, 604/218, 220
See application file for complete search history.

(56) References Cited

U.S. PATENT DOCUMENTS 2,464,840 A 3/1949 Fogg
5,053,010 A 10/1991 McGary et al.
(Continued)

FOREIGN PATENT DOCUMENTS

CA 2580092 A1 3/2009
EP 1092443 A2 4/2001
(Continued)

OTHER PUBLICATIONS

Foreign Communication From a Related Counterpart Application—International Search Report and Written Opinion, PCT/SG2010/000496, Apr. 26, 2011.
(Continued)

*Primary Examiner* — Manuel Mendez (57) ABSTRACT

A retractable syringe is proposed having a cutting head mounted on a plunger of the syringe. When the plunger is advanced to expel fluid from the syringe, the cutting crown cuts a retention mechanism which holds a needle unit of the syringe, allowing a drive mechanism to drive the needle unit into the syringe. The cutting crown is shaped to reduce the force which has to be applied to cut the retention mechanism. Furthermore, a disposable needle assembly for attachment to a syringe unit is proposed. The disposable needle assembly has a needle and connector element for connecting the needle to the syringe unit. The connector element encircles the needle and has a thread on its outer surface for mating with the syringe unit.

9 Claims, 9 Drawing Sheets

(56) References Cited

U.S. PATENT DOCUMENTS 6,409,701 B1  6/2002  Cohn et al.
8,864,706 B2 * 10/2014  Ang .................... A61M 5/3202
                                                    604/110

FOREIGN PATENT DOCUMENTS

| JP | H06503236 A | 4/1994 |
| JP | 2003512897 A | 4/2003 |
| WO | 2006044390 A1 | 3/2009 |
| WO | 2011139229 A1 | 11/2011 |

OTHER PUBLICATIONS

Foreign Communication From a Related Counterpart Application—International Preliminary Report on Patentability, PCT/SG2010/000496, Sep. 12, 2011.

Foreign Communication from a Related Counterpart Application, Russian Office Action dated Feb. 4, 2014, Application No. 2012149593/14.

Foreign Communication from a Related Counterpart Application, Japanese Office Action dated Dec. 17, 2013, Application No. 2013-509031.

* cited by examiner

SYRINGE ASSEMBLY AND A NEEDLE UNIT FOR ATTACHMENT TO A SYRINGE UNIT TO FORM A SYRINGE ASSEMBLY

CROSS-REFERENCE TO RELATED APPLICATIONS

This application is a continuation-in-part of and claims priority to U.S. application Ser. No. 14/494,602, filed on Sep. 24, 2014, which is a continuation of U.S. patent application Ser. No. 13/696,617, filed Nov. 7, 2012 to Ang and entitled "Retractable Syringe with a Cutting Crown," which is a filing under 35 U.S.C. 371 as the National Stage of International Application No. PCT/SG2010/000492, filed Dec. 31, 2010 and entitled "A Retractable Syringe with a Cutting Crown," which claims the benefit of and priority to both U.S. Provisional Patent Application No. 61/332,270, filed May 7, 2010 and entitled "Retractable Syringe with Self-Destruct Design" and U.S. Provisional Patent Application No. 61/373,926, filed Aug. 16, 2010 and entitled "Fittings for Syringe, Needles and Certain Other Medical Equipment, all of which are incorporated herein by reference in their entirety for all purposes.

TECHNICAL FIELD

The present invention relates to medical syringes. More particularly it relates to a retractable syringe, and to a disposable needle unit for attachment to a syringe unit to form a syringe assembly.

BACKGROUND

Syringe assemblies having a needle ("cannula") are commonly used for the delivery of fluids, e.g. medicaments, into patients, and/or for aspirating fluids from the patients. Desirably, these syringe assemblies can be operated by a single hand, so that a doctor or nurse is able to operate them while using his or her other hand for another purpose. The force required should not be very great, or the doctor or nurse's hand will become tired if many injections are performed. Furthermore, it is often undesirable for the same needle of the syringe assembly to be used for multiple patients, and several forms of syringe assemblies are known which prevent or discourage this.

A first form of syringe assembly comprises a disposable needle assembly consisting of a needle and a connector element. Using the connector element, the needle assembly is temporarily attached to a forward end of an elongate syringe unit, to form the syringe assembly. The syringe unit has a barrel, and a plunger movable forward within the barrel towards the needle assembly. A medicament fluid is located in a volume between a front face of the plunger and the needle assembly. The volume communicates with the inside of the needle, so that as the barrel is advanced the fluid is driven through the needle. When this happens, it is undesirable to have fluid leaking through the junction where the circumference of the front face of the plunger meets the walls of the barrel. In order to be compliant with the ISO 7886-1 standard, the syringe unit has to withstand a compression force resulting in an internal test pressure of 300 kPa (3 bars) without leaking. When the medicament has been dispensed, the needle assembly is removed and disposed of.

Examples of such syringe assemblies are the Luer Taper and Luer Lock designs standardized under ISO 594. The Luer Taper variant uses a press fit connection between the needle assembly and syringe unit that works using friction. Unfortunately, the needle assemblies are prone to loosening and dropping off the syringe unit. The Luer Lock variant seeks to resolve the problem of loosening associated with the Luer Taper by using a thread locking system. The Luer Lock however has a complicated design involving multiply nested interlocking portions. Specifically, the syringe unit has a conical spout encircled by an internally threaded collar. The connection element of the needle assembly carries an external thread for engaging the collar, and defines a cavity for receiving the spout. The connection element is inserted into the gap between the spout and the collar.

Both these syringe assemblies contain a large amount of dead space—i.e. volumes in the syringe assembly which contain medicament which cannot be expelled from the syringe assembly. There is typically dead space within the connector unit and/or the interface between the connector unit and syringe unit. This dead space is an issue of concern as the cost of medicament may be high. It is possible to reduce the size of the dead space by reducing the tolerances in the production process, but this increases the production cost of the syringe assembly.

Another known form of syringe assembly is a "retractable syringe", which comprises a syringe unit, a needle unit (which in some forms of the retractable syringe is just a needle, but in others is a needle and a "needle hub", i.e. an encircling body of material, typically molded plastics material) located at one end of the syringe unit, a retention mechanism for maintaining the position of the needle unit with respect to the syringe unit, and a drive mechanism. Operation of the syringe causes the retention mechanism to be disabled after the syringe assembly has been used to deliver a medicament, and the drive mechanism then drives the needle unit into the syringe unit, so that the needle is no longer exposed. Retractable syringes are illustrated in U.S. Pat. No. 6,994,690, WO 2005/053779, U.S. Pat. No. 6,494,863, US 2008/0033355 and U.S. Pat. No. 7,351,224. Another retractable syringe is the BD Integra Syringe marketed by Becton, Dickinson and Company of New Jersey, United States. This retractable syringe has a detachable needle, and uses a form of connection between the syringe unit and the needle reminiscent of the Luer Lock system. Experiments have found that it may take an "activation" force of about 55N in order to break the retention mechanism of a 1 ml version of the Integra syringe. This force is estimated to be over 5 times the compression force which the syringe unit has to withstand without leaking in order to achieve the ISO 7886-1 standard.

Some of the earlier retractable syringes have thus reduced the amount of "activation" force required by having more dead space within the syringe and/or by staggering the activation process. In cases where staggering is used, dead space may be required to provide room for the cascaded movement of the individual elements involved in the activation process. Therefore, most designs of retractable syringe have dead spaces, resulting in wastage of the medicament. In some designs air may be trapped in the dead space, and is hard to expel this air before the syringe assembly is used.

Furthermore, since the retention mechanism has to be strong enough to resist the urging force generated by the drive mechanism, the user has to apply an inconveniently large force to break the retention mechanism, and release the needle unit.

Furthermore, the needle unit, syringe unit, retention mechanism and drive mechanisms of many known retractable syringes have too many parts, leading to high production cost. Since retractable syringes are expensive, some users are tempted to try to re-use them, and there is little to prevent this since almost all components remain intact following operation of the device.

SUMMARY

Embodiments relate to a retractable syringe of the kind including a needle unit, a barrel, a plunger movable within the barrel towards the needle unit, a drive mechanism for driving the needle unit into the barrel, and a retention mechanism for retaining the needle unit with respect to the barrel. The plunger has a cutting crown at its forward end, for cutting the retention mechanism as the plunger is advanced, so that the drive mechanism retracts the needle unit into the barrel. The profile of the cutting crown may include one or more cutting teeth which cut a first portion of the retention mechanism before other portions of the cutting crown cut other portions of the retention mechanism. In other words, a user does not have to apply sufficient force to the plunger simultaneously to break all portions of the retention mechanism. This reduces the required activating force.

A piston rides on the front of the plunger, such that a volume for holding a medicament is defined between the piston and the needle unit. This piston comprises a weakened portion which is cut by the cutting crown before the cutting crown cuts the retention mechanism. The weakened portion comprises a plurality of notches in a surface of the piston.

The needle unit may consist of the needle alone. In certain embodiments it comprises both a needle and an encircling body of material (e.g. plastics material) which functions as a needle holder. The needle holder may be formed by molding.

Other embodiments relate to a disposable needle assembly for attachment to a syringe unit having a plunger movable within a barrel, to form a syringe assembly. The disposable needle assembly has a needle and connector element for connecting the needle to the syringe unit. The connector element encircles the needle and has a thread on its outer surface for mating with the syringe unit. The needle assembly has a central bore of substantially constant bore extending along the whole length of the needle assembly. Thus, there is very little dead space within the needle assembly itself.

Furthermore, when the needle assembly mates with the syringe unit, the central bore of the needle assembly meets a passage of the syringe unit having substantially the same bore and communicating with the barrel of the syringe unit. This substantially reduces dead space at the interface between the syringe unit and the needle assembly.

Before attachment to the syringe, the needle of the needle assembly is preferably encased in a protector formed (e.g. by molding) as a one-piece unit together with the hub. The protector may be connected to the hub by a frangible portion.

Features of the retractable syringe and disposable needle assembly are combinable by forming a syringe unit which mates with the needle assembly using an element which defines the passage, and such that when the needle assembly and element are connected together, they together play the role of the "needle unit".

Certain embodiments of the present invention may have the advantages of:
  having a design that may be simple and effective but yet resulting in almost no dead space within the assembly;
  having a simple design that may allow for simple tooling and production economy;
  having a compact design that may allow for an efficient material usage, thus resulting in a product that may be environmentally sound;
  having a design with a minimal part count as components may be fabricated as integrated parts, e.g. the needle protector and the needle hub may be made as a single piece;
  having minimized medication wastage as there is almost no dead space;
  allowing for the easy elimination of hazardous air bubbles as there is almost no dead space;
  preventing the trapping of air bubbles;
  allowing for easy inventory management as the needle assembly may be used with both retractable and conventional syringes;
  assuring the integrity of a virgin needle as the integrity is easily verified; and
  allowing for a tamper proof design that may prevent reuse or recycling.

BRIEF DESCRIPTION OF THE FIGURES

Embodiments of the invention will now be described, by way of example only, with reference to the accompanying drawings, in which.

DETAILED DESCRIPTION OF THE EMBODIMENTS

A Retractable Syringe

Figure 1:
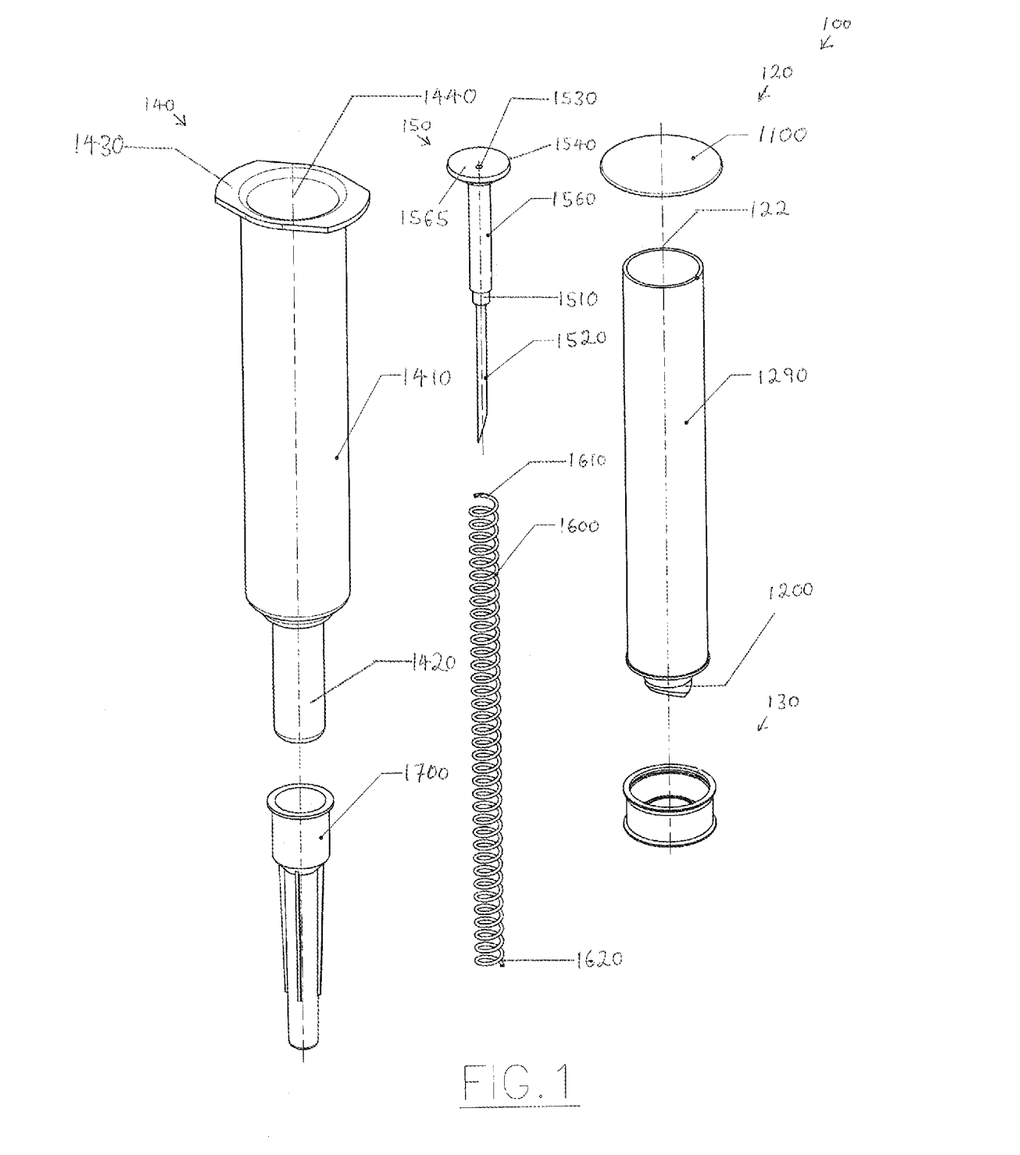
FIG. 1 is an exploded view of a syringe according to an embodiment.
Figures 2A, 2B, 2C, 2D:
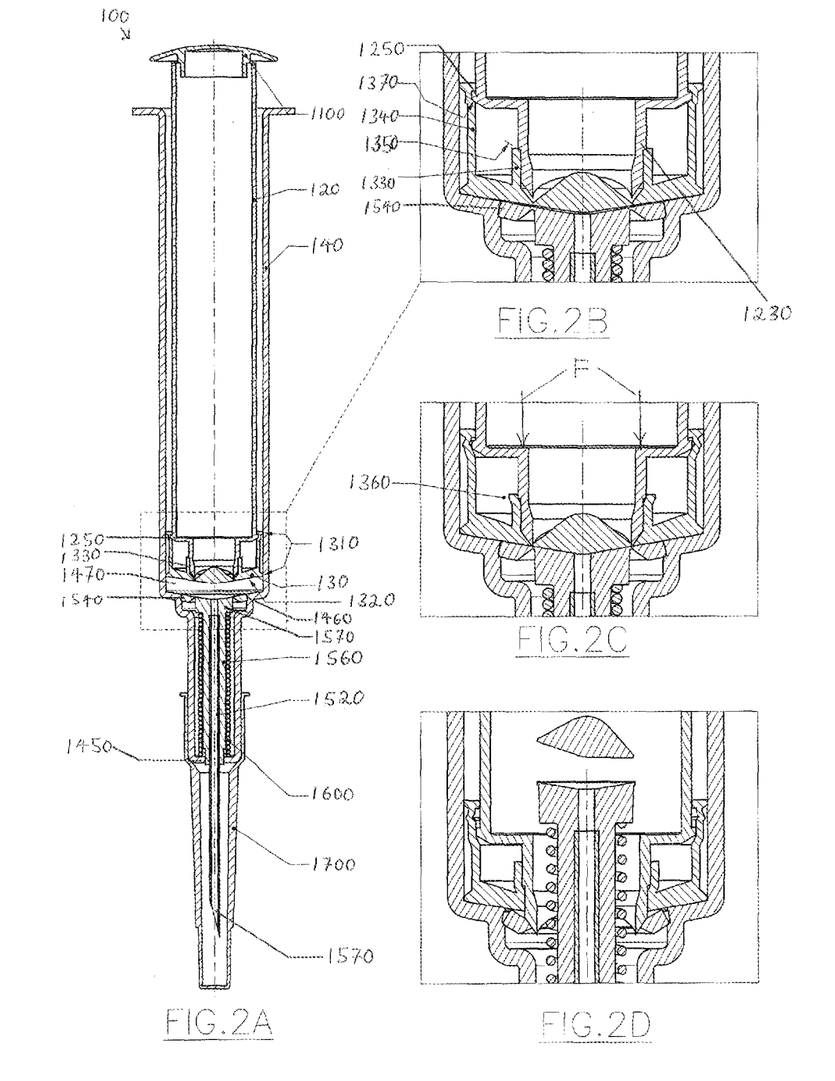
FIG. 2A is a cross-sectional view of the syringe of FIG. 1 when assembled.
FIG. 2B is a cross-sectional view of a piston of the syringe of FIG. 2A when the piston is proximate a retention mechanism.
FIG. 2C is a cross-sectional view of the piston as in FIG. 2B when a cutting crown of the syringe is brought to bear against a weak portion of the retention mechanism.
FIG. 2D is a cross-sectional view of the piston as in FIG. 2B after the cutting crown cuts the piston and the retention mechanism.

FIG. 1 is an exploded view of a syringe 100 according to embodiments of the present invention. FIG. 2A is a cross-sectional view of the syringe of FIG. 1 when assembled. The arts of the syringe 100 are described next with reference to FIGS. 1 and 2A.

The syringe 100 comprises a hollow barrel 140 defining a chamber, a plunger 120 insertable within the chamber, a piston 130 which is inserted into the chamber before the plunger 120, and a retraction assembly 150 to be fitted at a front portion 1420 of the barrel 140. The barrel 140 functions as a housing providing support to the other parts of the syringe 100, e.g. the retraction assembly 150. In different versions of the embodiment, the size of the barrel 140 differs, so as to have varying fluid capacities. In these various versions of the embodiment, the barrel 140 has differing diameters, and the diameters of the piston 130, plunger 120 and/or retraction assembly 150 also differ to suit the diameter of the barrel 140. A spring 1600 surrounds the needle holder 1560.

The retraction assembly 150 includes a needle 1520 and a needle holder 1560 which encircles the needle 1520. The needle holder 1560 is integral with a needle hub 1510 and with a seal 1540. The junction between needle hub 1510 and the seal 1540 is an annular weak portion 1590 (shown in FIG. 3D). As described below, the needle 1520, needle holder 1560 and needle hub 1510 together function as a needle unit which is eventually driven into the barrel 140, and the seal 1540 and annular weak portion 1590 function as a retention mechanism for retaining the needle unit relative to the syringe unit until the retention mechanism is disabled. Once this happens, the spring 1600 functions as a drive mechanism to drive the needle unit into the plunger 120.

Figure 9A:
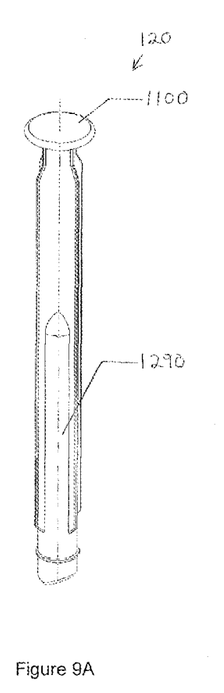
FIG. 9A is a perspective view of a variation of a plunger of the syringe of FIG. 1.
Figure 9B:
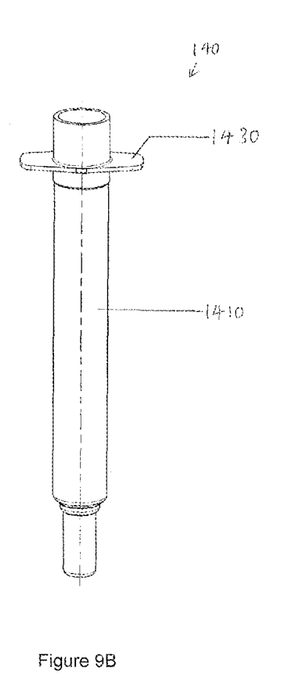
FIG. 9B is a perspective view of a variation of a barrel of the syringe of FIG. 1.

The barrel 140 comprises a hollow cylinder portion 1410, a mouth 1440 and the front portion 1420. The front portion 1420 may be tapered. The cylinder portion 1410 forms the main body of the syringe, thus permitting a user to hold the syringe steady in place when performing an injection. Optionally, the barrel 140 comprises one or more flanges 1430 for the purpose of providing additional holding surfaces. These flanges 1430 may be as shown in FIG. 1, situated at the mouth 1440 of the barrel away from the front portion 1420. Alternatively, the flanges 1430 may be situated anywhere along the external surface of the cylinder portion 1410 or even the front portion 1420. FIG. 9B is a perspective view of a variation of the barrel 140 where the flanges 1430 are disposed a suitable distance away from the mouth 1440. The distance is chosen to allow for a separation between the flanges 1430 and the exposed end of the plunger 120 which may allow a user to have a better grip of the syringe. Further, the skilled person will also understand that the flanges 1430 may take on other forms apart from that shown in FIGS. 1, 2A or 9B, for example taking the form of finger loops or an annular lip.

The plunger 120 comprises a stem 1290 with an end cap 1100 fitted over a top end of the plunger 120, and a cutting crown 1200 at the bottom end of the plunger 120. The stem 1290 is tubular. As described below, the tubular stem permits the retraction of the needle 1520 into stem 1290 and thus into the main body of the syringe 100. The purpose of the end cap 1100 is to improve a user's grip when the user is performing the push and pull pumping action associated with performing an injection. Further, the end cap 1100 may prevent the needle holder 1560 and/or needle 1520 from dropping out of the plunger 120 after the needle 1520 is driven into the plunger.

The end cap 1100 may also be suitable for a user to depress the plunger 120 within the barrel 140 with a thumb. Such an end cap 1100 may be made as a separate piece to be fitted onto the top end of the stem 1290 in which case the plunger 120 contains a retention means for holding the end cap 1100 in place. Optionally, as shown in FIG. 9A, the end cap 1100 may be made integrated with the stem 1290. FIG. 9A is a perspective view of a variation of the plunger 120 where the end cap 1100 and the stem 1290 is formed together as a singular item. By integrating the end cap 1100 together with the stem 1290, the part count may be lowered, thus allowing for a more efficient use of production material and an optimization of production cost.

Similarly, the cutting crown 1200 may be made either integrated as part of the plunger 120, or it may be made as a separate piece to be fitted at the bottom end of the plunger 120. The cutting crown 1200 will be described to a greater detail below.

The piston 130 is disposed over the cutting crown 1200. The piston 130 comprises a cylindrical portion 1340 which has an outer diameter slightly less than that of the inner diameter of the cylinder portion 1410 of the barrel 140, and further comprises one or more annular sealing lips 1310 running around the outer surface of the cylindrical portion 1340. The cylindrical portion 1340 forms a wall around the cutting crown 1200 when the piston 130 is disposed over the cutting crown 1200. The cylindrical portion 1340 provides support for the piston 130, thus allowing the piston 130 to withstand the compression forces exerted on the piston 130 when the plunger 120 is depressed. The sealing lips 1310 allow the piston 130 to have a tight fit within the body of the barrel 140 and may thus permit the proper expelling or aspiration of fluids out of or into the barrel 140. Further, the piston 130 may also be made out of a resilient material so achieve a tighter fit between the piston 130 and the barrel 140. The tight fit may help to ensure the proper expelling or withdrawing of liquid or gas by the syringe 100.

Figure 3A:
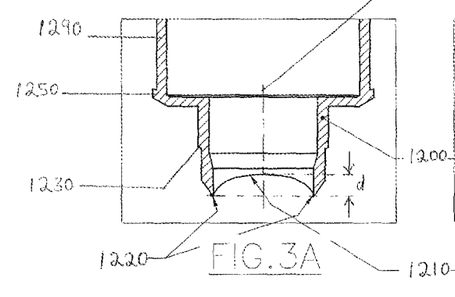
FIG. 3A is a cross-sectional view of the cutting crown of FIG. 2B.
Figure 3B:
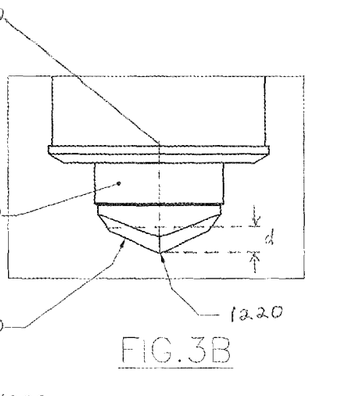
FIG. 3B is a side view of the cutting crown as in FIG. 3A.
Figures 3C, 3D, 3E, 3F:
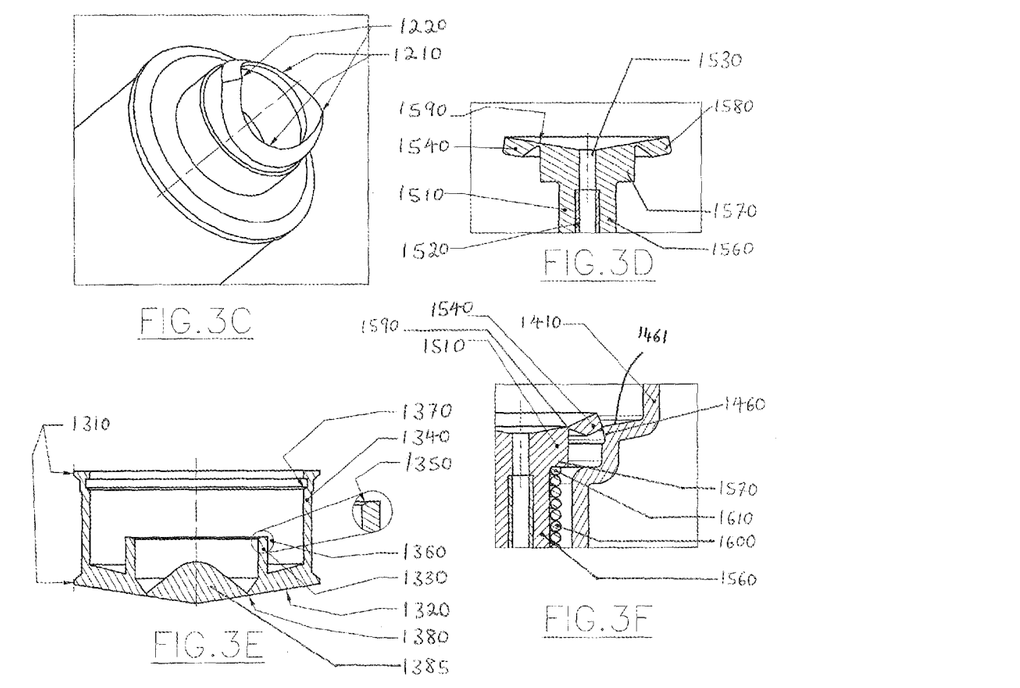
FIG. 3C is a perspective view of the cutting crown of FIG. 2B.
FIG. 3D is a cross-sectional view of a retraction assembly of the syringe of FIG. 1.
FIG. 3E is a cross-sectional view of the piston of FIG. 2B.
FIG. 3F is a cross-sectional view of a part of the retraction assembly of FIG. 3D when it is fitted into a front portion of a barrel.

The piston 130 will now be further described with the aid of FIG. 3E. FIG. 3E is a cross-sectional view of the piston 130. The piston 130 comprises a central domed elevated portion 1385, a weak portion 1380 forming a circumferential perimeter about the elevated portion 1385, and a guiding means 1330 extending inwardly from the inner surface of the piston 130. As described below, the piston 130 will be cut by the cutting crown 1200, and the weak portion 1380 reduces the effort required for cutting the piston 130.

The elevated portion 1385 serves to thicken the central portion of the piston 130. Thickening the central portion reinforces it and thus prevents an inward collapse of the piston 130 as it withstands the resistive forces exerted by the fluids contained within the barrel 140 when the plunger 120 is depressed. Further, having a domed shape for the elevated portion 1385 may serve to better diffuse the resistive forces, thus providing better reinforcement. It is noted that having such a reinforced piston 130 may also be advantageous as it serves to reduce the flexing of the piston 130 when the plunger 120 is depressed or withdrawn.

Turning now to the guiding means 1330, the guiding means 1330 may also provide support for the piston 130 so as to enable the piston 130 to withstand the compression forces exerted on the piston 130 when the plunger 120 is depressed. The elevated portion 1385 and the guiding means 1330 guide cutting teeth 1220 of the cutting crown 1200 towards the weak portion 1380. There may be any number of cutting teeth, but there are preferably in the range 2 to 5 such teeth. The guiding means 1330 may be annular with a chamfered edge 1350 facing away from the inner surface of the piston 130. A ledge 1230 of the cutting crown 1200 rests against the chamfered edge 1350 when the plunger 120 advances. Thus, the guiding means 1330 also plays the role of a spacer preventing the cutting teeth 1220 from prematurely cutting into the weak portion 1380 when the piston 120 is expelling fluid from the syringe 100. The chamfered edge 1350 may also aid in the guiding of the cutting teeth 1220 towards the weak portion 1380. Further, the guiding means 1330 may also play the role of a biasing means providing a biasing force against the cutting crown 1200 when the end of the plunger 120 approaches the seal 1540. Such a biasing means 1330 provides a tactile feedback to a user depressing the plunger 120 in the form of a "click". This allows the user to know when the cutting crown 1200 is about to bear against the weak portion 1380 of the piston 130 and the weak portion 1590. In such a case, after the cutting crown 1200 breaks the weak portion 1590, the biasing means 1330 may be deformed.

The outer cylindrical portion 1340 has a catch 1370 for retaining the piston 130 over the cutting crown 1200. This catch 1370 may take the form of an annular recess running around the inner surface of the cylindrical portion 1340 in which case the catch 1370 may also provide added rigidity to the piston 130, thus restricting any buckling of the piston 130 when a large compression force acts upon it. With reference to FIG. 2A, the catch 1370 may be mated with a ridge 1250 running around the cylindrical sides of the cutting crown 1200. Such a ridge 1250 and catch 1370 may permit the piston 130 to be retained over the plunger 120 when the plunger 120 is slid up or down the length of the barrel 140. The plunger 120 and piston 130 arrangement thus enables the push and pull pumping function for injecting or aspirating a fluid.

Figures 10A, 10B:
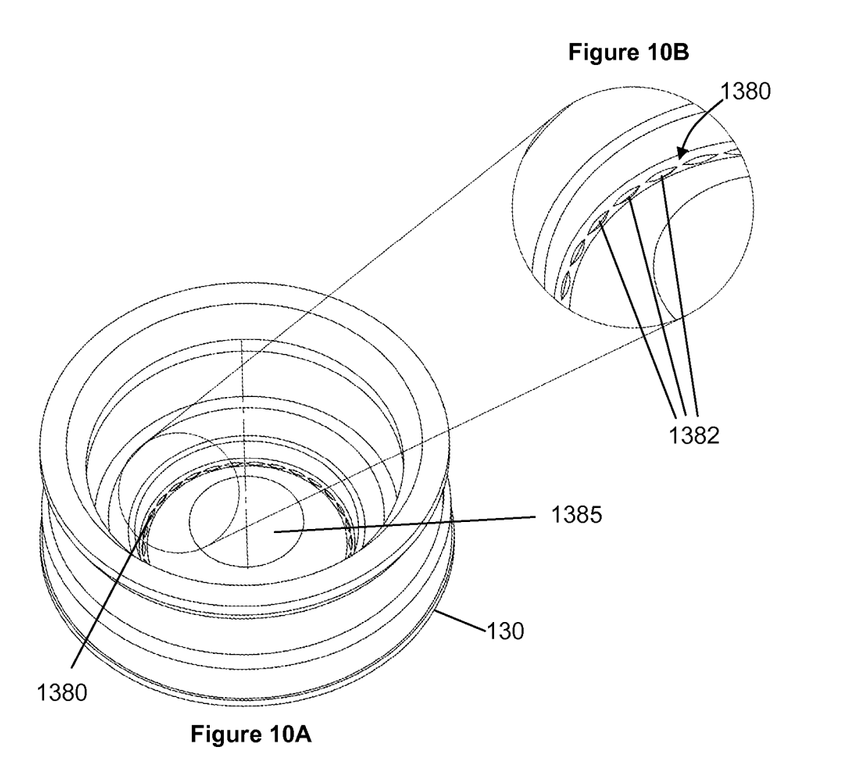
FIG. 10A shows a syringe piston of an embodiment.
FIG. 10B is an enlarged view of part of the syringe piston of FIG. 10A.

The weak portion 1380 of the piston 130 is shown in more detail in FIGS. 10A and 10B. In particular, weak portion 1380 comprises a plurality of notches 1382, forming a patterned blind perforation. That is, the notches 1382 do not penetrate completely through the surface of the piston 130 which is contacted by the cutting crown 1200.

The notches 1382 are formed as a series of blind apertures or blind furrows around the elevated portion 1385 of the piston 130, at a diameter which is less than the internal diameter of the cutting crown 1200. By providing a weak portion 1380 thus formed, a series of stress points is provided on the plunger 130 such that the plunger 130 is more easily cut by the cutting crown 1200, to allow the cutting crown 1200 to more readily proceed to rupture the retention means which retains the needle unit. Further, the cutting edge at the periphery of the elevated portion 1385 is smoother than if an unbroken annular weak portion is used. In addition, the ease of manufacturing the plunger 130 by molding is increased, as weak portion 1380 may be made significantly thicker.

Returning to FIGS. 1 and 2A, the inner dimensions of the mouth 1440 and the cylinder portion 1410 of the barrel 140 are made suitable for receiving the piston 130 and the plunger 120. In normal assembly, the piston 130 may be fitted to the plunger 120 before the plunger 120 is inserted into the barrel 140. Alternatively, optionally, the piston 130 and plunger 120 may be formed as a one-piece (i.e. integral) item. After the plunger 120 and piston 130 are inserted into the barrel 140, the plunger 120 and piston 130 are slideable within the barrel 140.

A passage 1530 runs through the needle holder 1560, so that the volume 1470 within the barrel 140 between (i) the piston 130, and (ii) the needle hub 1510 and seal 1540, communicates with the inside of the needle 1520. Otherwise, fluid cannot escape from the volume 1470.

FIGS. 3D and 3F respectively show a cross-sectional view of the retraction assembly 150, and a cross-sectional view of part of the retraction assembly 150 of FIG. 3D when it is fitted into the front portion 1420 of the barrel 140. The weak portion 1590 around the seal 1540 is frangible so that when it is broken, the needle holder 1560 will be released and be pushed upwardly by the spring 1600. The weak portion 1590 allows the cutting crown 1200 of the plunger 120 to break the retention mechanism formed by the weak portion 1590 and the seal 1540 with greater ease. Further, the thinness of the weak portion 1590 allows the seal 1540 to be flexed. By flexing the seal 1540, the retraction assembly 150 may be fitted more easily into the front portion 1420 of the barrel 140.

When the syringe 100 is assembled, the retraction assembly 150 is attached to the front portion 1420 of the barrel 140 by the outer surface 1580 of the seal 1540. The outer circumference 1580 comes to rest against the side wall of the front portion 1420. An annular recess 1460 may be formed into the inner wall of the front portion 1420 to function as a retaining means for holding the seal 1540. Such an annular recess 1460 may also have the advantage of creating a more water tight seal between the seal 1540 and the front portion 1420. An adhesive may also be applied around the outer circumference of the seal 1540 to create a tighter seal. Further, it is also envisaged that in variants of the embodiment, parts or the whole of the retraction assembly 150 may be formed integrated with the front portion 1420. As an example, the seal 1540 may be integrated with the front portion 1420 to form a single piece.

The spring 1600 is compressed within the front portion 1420 of the barrel 140. The spring 1600 may be attached at a first end 1610 to the needle holder 1560 and at the other end 1620 attached to the front portion 1420 of the barrel 140. The needle holder 1560 comprises one or more anchor points 1570 holding the end 1610 of the spring 1600. The anchor point 1570 may take the form of a ledge with an outer diameter wider than that for the spring 1600. In such a case, the end 1610 may rest upon the anchor point 1570, the anchor point 1570 thus providing a point of resistance which permits the spring 1600 when compressed to push the needle holder 1560 upwardly.

At the other end 1620 of the spring 1600, the end 1620 of the spring 1600 bears against an annular lip 1450 of the front portion 1420. The annular lip 1450 provides a point of support which the compressed spring 1600 pushes against. The compressed spring 1600 thus expands and pushes in opposite directions against the annular lip 1450 and the anchor point 1570.

Returning to FIGS. 1 and 2A, the syringe 100 optionally further comprises a needle protector 1700. Such a needle protector 1700 may be fitted over the front end 1420 of the barrel 140. The protector 1700 has a retention means for keeping the protector 1700 in place over the front end 1420 and the needle 1520.

The cutting crown 1200 will now be further described with the aid of FIGS. 3A, 3B and 3C. FIG. 3A is a cross-sectional view of the cutting crown 1200. FIG. 3B is a side view of the cutting crown 1200 of FIG. 3A. FIG. 3C is a perspective view of the cutting crown 1200 of FIG. 3A.

The cutting crown 1200 comprises a ledge 1230 that rubs against the chamfered edge 1350 of the piston 130 as the cutting teeth 1220 approach the seal 1540. The cutting crown 1200 further comprises one or more cutting teeth 1220 located at the leading end of the plunger 120. These cutting teeth 1220 are arranged circumferentially around the longitudinal axis 122 of the plunger 120 and taper inwardly towards the longitudinal axis 122. The edge of the teeth 1220 may be chamfered to yield a sharpened cutting edge suitable for cutting into the weak portion 1380 of the piston 130 and the weak portion 1590 of the retraction assembly 150. The teeth 1220 are thus be capable of cutting the piston 130 and the weak portion 1590 with a minimal amount of effort. Interspaced between each consecutive cutting tooth 1220 along the cutting edge are bridges 1210. Each bridge 1210 may have an arcuate profile spanning from tooth to tooth. When the cutting crown 1200 is brought to bear against the piston 130 and/or the weak portion 1590, such an arcuate profile may result in a better diffused distribution of resistive forces acting upon each tooth 1220, thus resulting in teeth 1220 that are stronger and better able to cut through the piston 130 and/or the weak portion 1590.

When designing the cutting crown 1200, a cutting distance d (as indicated in FIG. 3A) and a puncturing force F (as indicated in FIG. 2C) may be minimized. As is illustrated in FIGS. 3A and 3B, the cutting distance d is defined as the perpendicular distance from the apex of the teeth 1220 to the nadir of the bridge 1210. The puncturing force F is defined as the force required for the teeth 1220 of the cutting crown 1200 to cut the piston 130 and/or the retraction assembly 150.

A short cutting distance d may be advantageous because it means a user will have to provide a sustained cutting force on the plunger 120 for a shorter sliding distance. A lesser puncturing force F may be advantageous because it means the user will have to provide less instantaneous force to pierce into the piston 130 and/or the retraction assembly 150.

Figure 7:
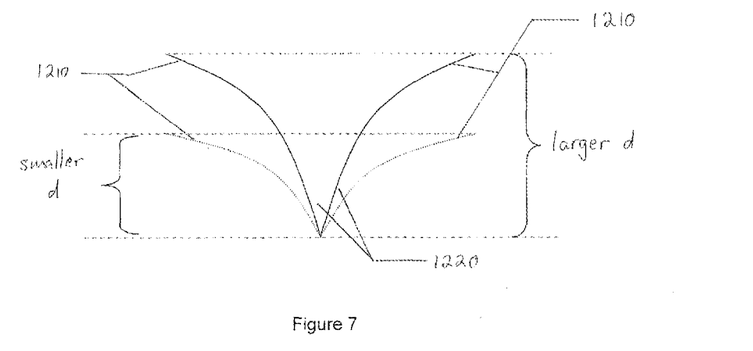
FIG. 7 is a schematic drawing showing two teeth of the cutting crown of FIG. 2B with different cutting distances.

There exists a trade-off between the cutting distance d and the puncturing force F. FIG. 7 shows two possible profiles for bridges 1210 and tooth 1220, each profile having a different value of d. It can be seen that lower values of d are associated with lower sharpness of the tooth 1220. The reduced "sharpness" of each tooth 1220 however is undesirable as it requires a greater puncturing force F. Consequently, in order to have a lower puncturing force F, the distance d may be made larger in order to increase the "sharpness" of the tooth 1220.

Figure 8A:
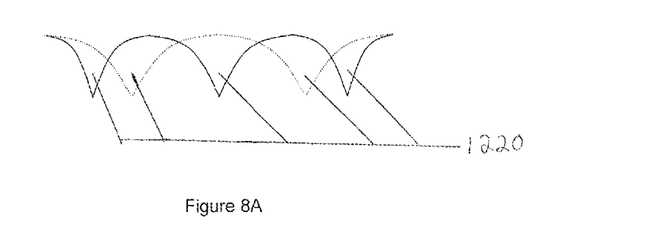
FIG. 8A is a schematic side view of the cutting crown of FIG. 2B with five cutting teeth.
Figure 8B:
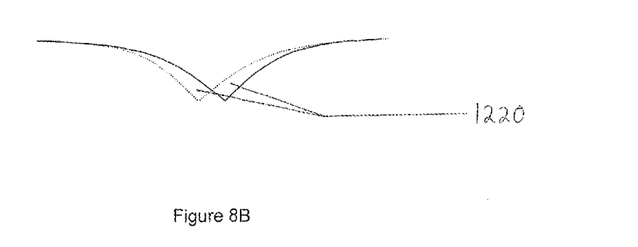
FIG. 8B is a schematic side view of the cutting crown as shown in FIG. 8A but with two cutting teeth.

Holding the cutting distance d constant, the "sharpness" of each tooth 1220 may be improved by increasing the number of teeth 1220 arranged around the end of the plunger 120. FIG. 8A shows a side view of a cutting crown 1200 with five cutting teeth 1220 (the solid lines in FIG. 8A show the port of the cutting crown which face the viewer, while the dashed portions show the part of the cutting crown facing away). FIG. 8B shows an alternative cutting crown 1200 with two cutting teeth 1220. It can be seen that the teeth 1220 of FIG. 8A are "sharper" than the teeth 1220 of FIG. 8B.

It is thus noted that there exists a further trade-off between the number of teeth 1220 and the puncturing force F. While having more cutting teeth 1220 may result in "sharper" teeth 1220, it also results in the puncturing force F having to be greater because it is divided between a greater number of teeth 1220. Thus in the interest of having a lesser puncturing force F, a lesser number of cutting teeth 1220 may be employed.

The typical operation of the assembled syringe 100 is next described with reference to FIGS. 2A to 2D. FIG. 2A is a cross-sectional view of the assembled syringe 100 before it is used. FIG. 2B is a cross-sectional view of the piston 130 when the piston 130 is proximate the seal 1540. FIG. 2C is a cross-sectional view of the piston 130 when the cutting crown 1200 is cutting the weak portion 1380 of the piston 130. Finally, FIG. 2D is a partial cross-sectional view of the piston 130 after the cutting crown 1200 has cut the piston 130 and the weak portion 1590.

A user of a fresh syringe 100 first removes the needle protector 1700. The tip 1570 of the needle may be placed in a fluid e.g. a medicament that is to be drawn into the syringe 100. The plunger 120 is then withdrawn from the barrel 140. This may be done by the user using a first hand to firmly grasp the outer surface of the barrel 140 while using a second hand to hold the end cap 1100 and draw back the plunger 120.

The syringe 100 has a space 1470 that is formed within the barrel 140 between an outer surface of the piston 130 facing away from the cutting crown 1200 and the top face 1565 of the needle holder 1560. When the plunger 120 is withdrawn from the barrel 140, the increase in the volume of the space 1470 sucks fluid into the space 1470. The fluid is fed into the space 1470 via the passage 1530 leading through the needle holder 1560 of the retraction assembly 150.

The user then depresses plunger 120 in order to expel the fluid from the syringe 100. This may be done by the user grasping the outer surface of the barrel 140 with the index finger and the middle finger of a hand, while using the thumb of the hand to press against the end cap 1100. The flanges 1430 aid this action as they provide additional holding surfaces for the index and middle finger.

When the plunger 120 is depressed, the piston 130 forces the fluid contained within the space 1470 out via the passage 1530. The outer surface 1320 of the piston 130 that faces away from the cutting crown 1200 has a domed profile which matches the concave receiving surface disposed at the front portion 1420 of the barrel 140. The receiving surface consists of the top face 1565 of the needle holder 1560, the seal 1540 and the end wall 1461 of the cylinder portion 1410 of the barrel 140. By having such a concave receiving surface, the syringe 100 may have the advantage of being easier to "bleed". What this means is that air bubbles contained within the space 1470 may be removed via the passage 1530 more easily. Also, the receiving surface is smooth and there are no gaps or protruding seams at the points where the top face 1565 of the needle holder 1560 meets the seal 1540, and where the seal 1540 meets the end wall 1461 of the barrel 140. Such a smooth surface may further contribute to the advantage of being easier to "bleed" as there will be an absence of irregularities on the surface which may retain air bubbles.

The process of "activating" the syringe 100 is described next across three "activation" states. Referring now to FIG. 2B, the plunger 120 is depressed until the cutting crown 1200 is approaches the weak portion 1380 of the piston 130. The ledge 1230 of the cutting crown 1200 rubs against the chamfered edge 1350 of the piston 130 and the guiding means 1330 provides a tactile feedback to a user depressing the plunger 120 in the form of a "click". When this happens, the syringe 100 is in the first "activation" state and the guiding means 1330 is also forced outwardly away from the longitudinal axis 1440. This frees the guiding means 1330 from its role as a spacer preventing the cutting crown 1200 from prematurely cutting the weak portion 1380. Further, the cylindrical portion 1340 may be deformed as the ridge 1250 runs down the inside of the piston 130. As the plunger 120 is further depressed, the elevated portion 1385 and the guiding means 1330 guide the one or more cutting teeth 1220 of the cutting crown 1200 towards the weak portion 1380. It is estimated that the force required to achieve the first "activation" state may be about 1.2 to 2 times the compression force which the syringe has to withstand without leaking in order to achieve the ISO 7886-1 standard.

During this process, a radially-outer portion of the front surface 1320 of the piston 160 first meets the end wall 1461 of the cylinder portion 1410 of the barrel 140. Gradually, more radially-inward portions of this surface 1320 contact the end wall 1461 of the portion 1410, and then the seal 1540 and top face 1565 of the needle holder 1560. In other words, the contact area of the plunger with the end of the chamber gradually expands radially-inwardly. When the syringe 100 is emptied, the top face 1565 fully meets the outer surface 1320. This may assist in fully expelling the fluids contained within the space 1470, thus preventing as fluid wastage.

Turning now to FIG. 2C, the plunger 120 is depressed further until the cutting crown 1200 cuts through the weak portion 1380 of the piston 130. The syringe 100 is now in the second "activation" state. The application of the puncturing force F on the plunger 120 forces the cutting teeth 1220 to pierce into the weak portion 1380 of the piston 130 and thereafter also cuts through the weak portion 1590 of the retraction assembly 150.

Referring now to FIG. 2D, the plunger 120 is depressed even further for a cutting distance d, at which time syringe 100 is in the "third" activation state and the sharpened cutting edge of the teeth 1220 cuts completely through the weak portion 1590. When this happens, the retention mechanism formed by the weak portion 1590 and the seal 1540 can no longer retain the needle unit (i.e. the needle 1570, the needle holder 1560 and the hub 1510). Furthermore, the elevated portion 1385 has been released from the main body of the piston 130. This permits the needle unit to be pushed upwards by the spring 1600 and into the stem 1290 of the plunger 120. When doing so, the spring 1600 also pushes the released elevated portion 1385 into the stem 1290. The spring 1600 is allowed to expand to its maximum extend thus bringing the needle holder 1560 and any attached needle 1520 entirely within the stem 1290. The needle holder 1560 and attached needle 1520 are thus retracted into the syringe 100. The syringe 100 in this state may thus be said to have been "activated". It is noted that the force needed to complete the cut through the weak portion 1590 in the "third" activation state may be less than the puncturing force F.

It is noted that once the syringe 100 has been "activated", the piston 130 and the retraction assembly 150 are destroyed. The syringe 100 thus may no longer be reused and this may prevent the recycling of syringes.

Figure 4:
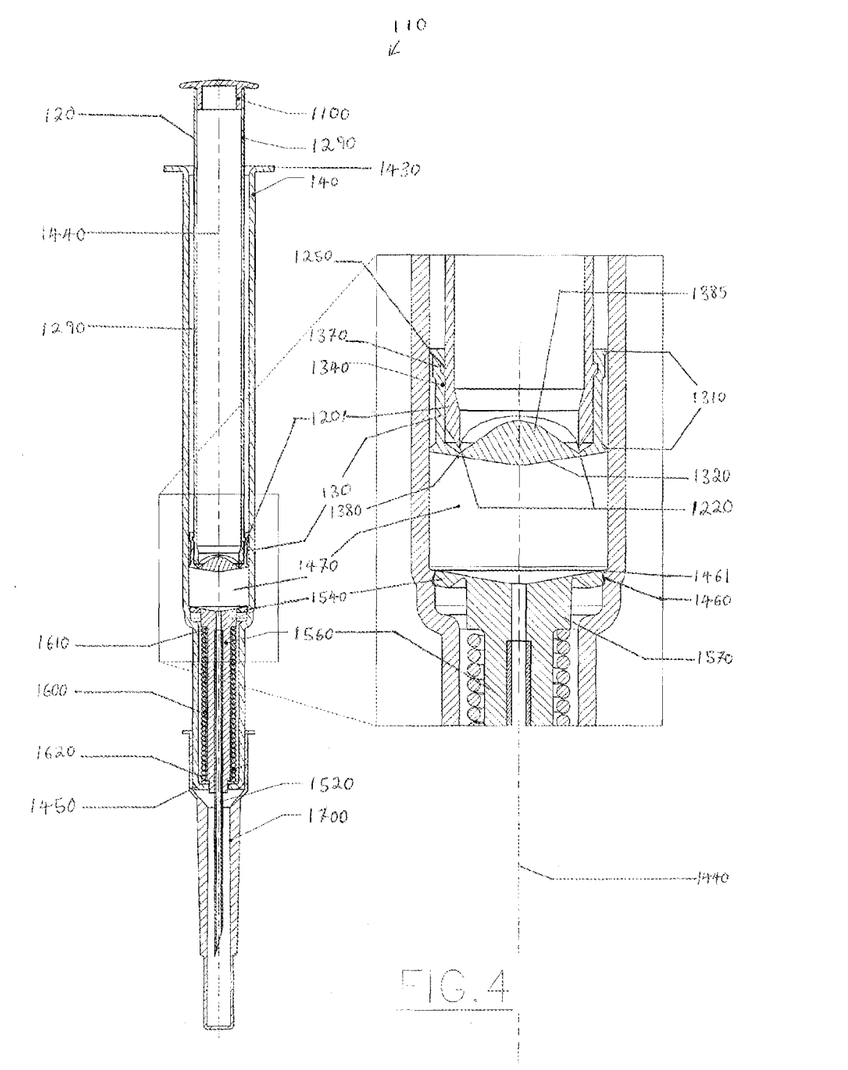
FIG. 4 is a cross-sectional view of an assembled syringe according to an embodiment.

A second embodiment of the present invention is described next with the aid of FIG. 4. FIG. 4 is a cross-sectional view of an assembled syringe 110 according to a second embodiment of the present invention. The syringe 110 may be especially suitable for small fluid volumes (e.g. 1 ml or 10 ml), but may also be used with any other volume of fluid. The second embodiment has elements in common with the first embodiment and these like elements are designated using like reference numerals.

The second embodiment differs from the first embodiment by having a wider cutting crown 1201 of a diameter that is substantially the same as that for the stem 1290. Conspicuously, the guiding means 1330 previously present in the second embodiment is now absent and the end wall 1461 is now reduced to an annular ledge. The roles previously played by the guiding means 1330 may now be fulfilled by the outer cylindrical portion 1340 of the piston 130.

The syringe 110 may be operated the same way as the syringe 100. When "activating" the syringe 110, in the first "activation" state i.e. when the plunger 120 is depressed until the cutting crown 1201 approaches the weak portion of the piston 130, the lower of the sealing lips 1310 comes to rest against the end wall 1461. The piston 130 is thus restricted from travelling further down the barrel 140. The cylindrical portion 1340 now performs the role of a spacer preventing the cutting crown 1201 from prematurely cutting the weak portion 1380.

A further application of downward pressure dislodges the ridge 1250 from the catch 1370, thus permitting the cutting crown 1201 to travel downwardly free of the piston 130. The dislodgment of the ridge 1250 from the catch 1370 may result in a tactile feedback to the user in the form of a "click". As the cutting crown 1201 travels downwardly towards the weak portion 1380 of the piston 130, the elevated portion 1385 and the cylindrical portion 1340 guide the one or more cutting teeth 1220 of the cutting crown 1201 towards the weak portion 1380. Meanwhile, the ridge 1250 also deforms the cylindrical portion 1340 outwardly away from the longitudinal axis 1440 as it travels down the cylindrical portion 1340.

As in the case of the first embodiment i.e. the syringe 100, the downward travel of the cutting crown 1201 causes the one or more cutting teeth 1220 of the cutting crown 1201 to eventually bear against the weak portion 1380 of the piston 130. The second "activation" state is thus arrived at. In the second and third "activation" states, the further functioning of the elements of the syringe 110 are the same as that for the syringe 100.

Figures 5A, 5B, 5C:
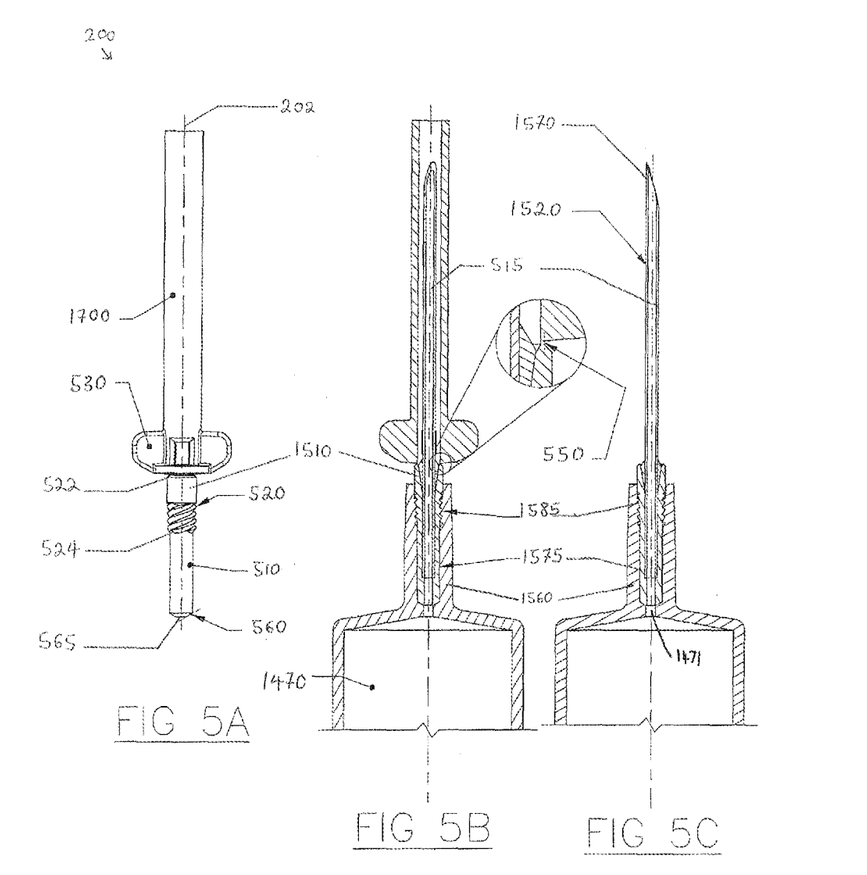
FIG. 5A is a drawing of a needle assembly according to an embodiment.
FIG. 5B is a cross-sectional view of the needle assembly of FIG. 5A installed onto a syringe unit.
FIG. 5C is a cross-sectional view of the needle assembly of FIG. 5B but with a needle protector removed.

We now turn to a third embodiment of the invention, which is a needle assembly 200. The needle assembly 200 will be described with reference to FIGS. 5A to 5C. FIG. 5A is a needle assembly 200 in its initial state. FIG. 5B is a cross-sectional view of the needle assembly 200 of FIG. 5A when installed onto a syringe. FIG. 5C is a cross-sectional view of the needle assembly 200 of FIG. 5B but with a protector 1700 portion removed.

The needle assembly 200 comprises a needle hub 1510 with threads 520 on the outer side wall, a needle (cannula) 1520 extending from a first end 522 of the hub 1510 to a distal tip 1570, and a tubular neck 510 that is suitable for insertion into the needle holder 1560 of a syringe extending from a second end 524 of the hub. A cylindrical bore 515 runs continuously length-wise through the center of the needle 1520 from the tip 1570, and on through the center of the hub 1510, and further on through the center of the neck 510 before terminating as an opening 565 at an end face 560 of the neck 510. The bore 515 functions as a conduit for the delivery of fluids from the syringe out through the tip 1570.

The needle 1520 may be made out of a metal e.g. stainless steel, or optionally other materials such as a rigid plastic. The tip 1570 of the needle 1520 may be chamfered and sharpened to assist in piercing surfaces. Optionally, the needle 1520 extends through the first end 522 of the hub 1510 and part of the way through the neck 510. In other embodiments, the needle 1520 may extend through the entire length of the needle assembly 200 from the tip 1570 to the end face 560. In either case, the bore 515 has a substantially constant shape (typically a circle) and size along its length, making it possible to much reduce any dead spaces.

The hub 1510 is cylindrical and has one or more nested helical threads 520 running on at least part of the outer cylindrical side wall of the hub 1510.

The threads 520 of the hub 1510 mate with corresponding threads 1585 present on the inner surface of the needle holder 1560. It is however envisaged that in a variant of the embodiment, the hub 1510 may not necessarily use a twist-locking system in order to mate the hub 1510 with the needle holder 1560. For example, a stopper based locking system may be used.

The neck 510 has a smooth outer surface. The neck 510 terminates with the end face 560 which may be beveled circumferentially so as to allow an easier fitting of the neck 510 into the needle holder 1560. The smooth outer surface of the neck 510 may function as a guiding surface leading the corresponding threads 1585 to the threads 520. Further, the neck 510 may result in a more secure seal, thus preventing the leaking of fluids originating from a passage 1471 of the syringe.

As mentioned above, the needle assembly 200 comprises a needle protector 1700 that is disposed over the needle 1520, thus encasing the needle 1520. Such a needle protector 1700 may prevent the needle 1520 from becoming a sharps hazard. It is envisaged that the protector 1700 may be formed as a single piece together with the hub 1510 in which case the protector 1700 may be connected to the hub 1510 by a frangible portion 550. Such a single piece design may confer the advantage of manufacturing ease, and a tamper proof needle assembly 200. The integrity of a virgin needle assembly 200 with the frangible portion 550 intact may thus be assured.

The frangible portion 550 is intended to break easily when a user twists the protector 1700 away relative to the hub 1510. The protector 1700 may further comprise one or more wings 530 extending from the outer wall of the protector 1700. The wings 530 may permit a user to better deliver rotational force to the protector 1700 about the longitudinal axis 202 of the protector 1700 when the protector 1700 is encasing the needle 1520. The skilled person however will understand that the wings 530 may take on other forms apart from that shown in FIGS. 5A and 5B, for example taking the form of finger loops or simply just a roughened surface.

The needle protector 1700 may further comprise a biasing means for holding onto the needle 1520 when the protector 1700 is encasing the needle 1520. Such a biasing means may be disposed internally within the protector 1700 and may serve to prevent the protector 1700 falling off the needle 1520 after the frangible portion 550 is broken.

The needle holder 1560 comprises a tubular recess 1575 that is suitable for receiving the needle assembly 200. The internal surface of the recess 1575 has a threaded portion containing threads 1585 which correspond to the threads 520 of the needle assembly 200.

It is noted that the hub 1510 of the needle assembly 200 has the form of a male body with outer threads 520, and the needle holder 1560 of the syringe has the recess 1575 which results in a female body with inner threads 1585. This results in a needle assembly 200 and needle holder 1560 that are easier to manufacture since the interlocking portions of both the needle assembly 200 and the needle holder 1560 i.e. the hub 1510 and the recess 1575 respectively, are not multiply nested when mated. Also, the compact design of the needle assembly 200 may require less material when manufacturing, thus allowing for more efficient material usage.

The needle assembly 200 may be installed into the syringe by inserting the neck 510 of the needle assembly 200 into the tubular recess 1575 first. The neck 510 is inserted past the inner threads 1585 until where the outer threads 520 of the needle assembly 200 are ready to be screwed onto the inner threads 1585.

The user may then screw the outer threads 520 of the needle assembly 200 onto the inner threads 1585 by holding onto the wings 530 of the protector 1700 and twisting. Such a mating of the outer threads 520 with the inner threads 1585 may be described as a "lock" because the interlocking threads may prevent the leakage of any fluid. Once the needle assembly 200 is fully inserted in the needle holder 1560, the hub 1510 of the needle assembly 200 may twist no further. By further twisting the protector 1700, the user delivers rotational force to the protector 1700 about the longitudinal axis 202 of the protector 1700. The rotational force breaks the frangible portion 550 connecting the protector 1700 to the hub 1510. When this happens, the protector 1700 becomes free from the rest of the needle assembly 200 and may be removed. The further twisting action that is used to break the frangible portion 550 may also assist in lodging the outer threads 520 together with the inner threads 1585 more tightly.

The recess 1575 is in fluid communication with the cylindrical chamber 1470 of the barrel 140 through the passage 1471. Thus when the needle assembly 200 is fully inserted into the recess 1575, the opening 565 of the end face 560 coincides with the passage 1471. The fact that the opening 565 of the end face 560 faces the passage 1471 and has substantially the same narrow diameter, prevents the existence of a dead space between the end face 560 of the needle and the passage 1471. A substantially constant bore 515 is formed from the space 1470 in the barrel 140 of the syringe 100, through the passage 1471, into the opening 565 of the needle assembly 200 and out through the tip 1570 of the needle 1520. Such a continuous bore 515 reduces dead spaces within the entire delivery channel since the diameter of each section of the continuous bore 515 may be similar. Also, the uniform diameter avoids trapping of air within the bore 515. The continuous bore 515 may also be made to be thin so as to reduce the amount of residual fluid present in the delivery channel when the syringe 100 is fully depressed.

It is noted that once the needle assembly 200 is installed onto the needle and the protector 1700 is broken free of the needle hub 1510, there may be no practical way for unscrewing the needle assembly 200 from the syringe 100 as the protector 1700 which provides traction for a user to twist the needle assembly 200 is now free of the needle hub 1510. This may thus also discourage the recycling of the needle assembly 200.

Figure 6:
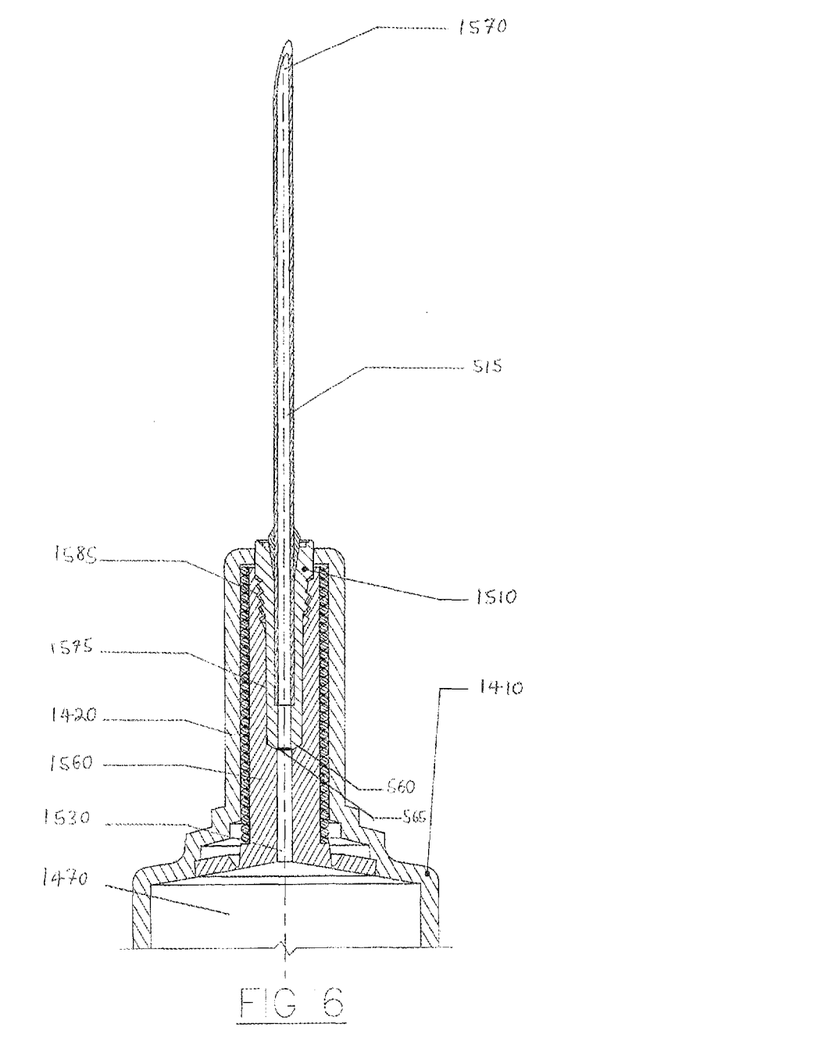
FIG. 6 is a cross-sectional view of an embodiment including a portion of the needle assembly of FIG. 5A.

A fourth embodiment of the invention is shown in cross-section in FIG. 6. The needle assembly of FIG. 6 is the third embodiment shown in FIG. 5A, but the syringe is a variant of the syringe 100 of FIG. 1, having corresponding portions labeled by the same reference numbers. In this variant, the retraction assembly 150 of FIG. 1 is replaced by a structure which is formed by inserting the needle assembly of FIG. 5A into a needle holder 1560. The operation of this embodiment is then the same as that of the first embodiment, except that the "needle unit" which is drawn into the syringe unit is composed of the needle 1570, and the needle hub 1510, and the needle holder 1560. Note that since the needle assembly 200 is usable both in the context of a retractable syringe (as in FIG. 6) and a non-retractable syringe (as in FIG. 5B) only a single type of needle assembly needs to be stocked to enable both these functions.

In this specification, the terms "needle" and "cannula" have been used interchangeably to refer to the needle 1520. Further, the term "fluid" may refer to either a "liquid" or a "gas".

Whilst example embodiments of the invention have been described in detail, many variations are possible within the scope of the invention as will be clear to a skilled reader.

The invention claimed is:

1. A retractable syringe comprising:
a barrel;
a needle unit comprising a needle, an interior of the needle being in fluid communication with a chamber within the barrel;
a retention mechanism for retaining the needle unit at one end of the barrel;
a hollow plunger movable within the barrel towards the needle unit;
a drive mechanism for driving the needle unit into the plunger; and
a cutting crown at the end of the plunger facing the needle unit, the cutting crown being arranged for cutting the retention mechanism as the plunger is advanced, so that the drive mechanism retracts the needle unit into the barrel;

wherein a piston is disposed over the cutting crown, and the piston has a weakened portion which is arranged to be cut by the cutting crown before the cutting crown cuts the retention mechanism; and wherein the weakened portion comprises a plurality of notches.

2. A retractable syringe according to claim 1, wherein the profile of the cutting crown comprises one or more cutting teeth which cut a first portion of the retention mechanism before other portions of the cutting crown cut other portions of the retention mechanism.

3. A retractable syringe according to claim 2 wherein the one or more cutting teeth taper inwardly towards a longitudinal axis of the plunger.

4. A method for operating a retractable syringe according to claim 2, the method including:
   depressing the plunger within the barrel, whereby the cutting teeth cut at least one first portion of the retention mechanism, and subsequently other portions of the cutting crown cut one or more second portions of the retention mechanism which are spaced from the first portions circumferentially around an axis of the barrel.

5. A retractable syringe according to claim 1 wherein the outer surface of the piston has a domed profile, and upon the plunger being moved towards the needle unit, the piston contacts an end surface of the chamber at a contact area, said contact area gradually expanding towards a central axis of the chamber.

6. A retractable syringe according to claim 1 further comprising a guiding means extending inwardly from the inner surface of the piston, the guiding means suitable for guiding the one or more cutting teeth towards the weakened portion of the piston.

7. A retractable syringe according to claim 1 wherein the weakened portion of the piston forms an annular perimeter about a central portion of the piston.

8. A retractable syringe according to claim 1 wherein the guiding means is deformed when the cutting crown breaks the seal.

9. A retractable syringe according to claim 1 in which the needle unit comprises:
   a needle holder having an inwardly facing threaded surface, and
   a needle assembly comprising a needle and a needle hub surrounding the needle and having an outwardly facing threaded surface;
   an aperture of the needle assembly facing a passage of substantially the same bore defined by the needle holder and extending into the chamber in the barrel.

* * * * *